(12) United States Patent
Faase et al.

(10) Patent No.: US 7,619,805 B2
(45) Date of Patent: Nov. 17, 2009

(54) LIGHT MODULATOR DEVICE

(75) Inventors: Kenneth J. Faase, Corvallis, OR (US); Adel Jilani, Corvallis, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 598 days.

(21) Appl. No.: 11/093,835

(22) Filed: Mar. 29, 2005

(65) Prior Publication Data
US 2006/0227404 A1  Oct. 12, 2006

(51) Int. Cl.
*G02B 26/00* (2006.01)
*G02B 26/08* (2006.01)
*G02F 1/29* (2006.01)

(52) U.S. Cl. .................. 359/290; 359/291; 359/292; 359/298

(58) Field of Classification Search ............ 359/290, 359/291, 292, 295, 296, 298
See application file for complete search history.

(56) References Cited

U.S. PATENT DOCUMENTS

| | | | | |
|---|---|---|---|---|
| 5,661,591 A * | 8/1997 | Lin et al. | | 359/290 |
| 6,172,797 B1 * | 1/2001 | Huibers | | 359/291 |
| 6,373,632 B1 | 4/2002 | Flanders | | |
| 7,026,695 B2 * | 4/2006 | Yang et al. | | 257/414 |
| 7,126,741 B2 * | 10/2006 | Wagner et al. | | 359/290 |
| 7,320,899 B2 * | 1/2008 | Haluzak et al. | | 438/31 |
| 2002/0015215 A1 | 2/2002 | Miles | | |
| 2005/0195370 A1 * | 9/2005 | Gore et al. | | 353/31 |
| 2006/0056004 A1 * | 3/2006 | Jilani et al. | | 359/291 |
| 2006/0119922 A1 * | 6/2006 | Faase et al. | | 359/290 |
| 2006/0203325 A1 * | 9/2006 | Faase et al. | | 359/290 |

FOREIGN PATENT DOCUMENTS

| | | |
|---|---|---|
| EP | 0 419 853 A | 4/1991 |
| WO | WO 03/007049 A | 1/2003 |
| WO | WO 2006/006200 A | 6/2006 |

* cited by examiner

*Primary Examiner*—Ricky L Mack
*Assistant Examiner*—Brandi N Thomas

(57) ABSTRACT

A light modulator device includes a bottom charge plate, a top charge plate, and a pixel plate supported by at least one flexure, wherein the flexure is a piece-wise linear flexure.

46 Claims, 15 Drawing Sheets

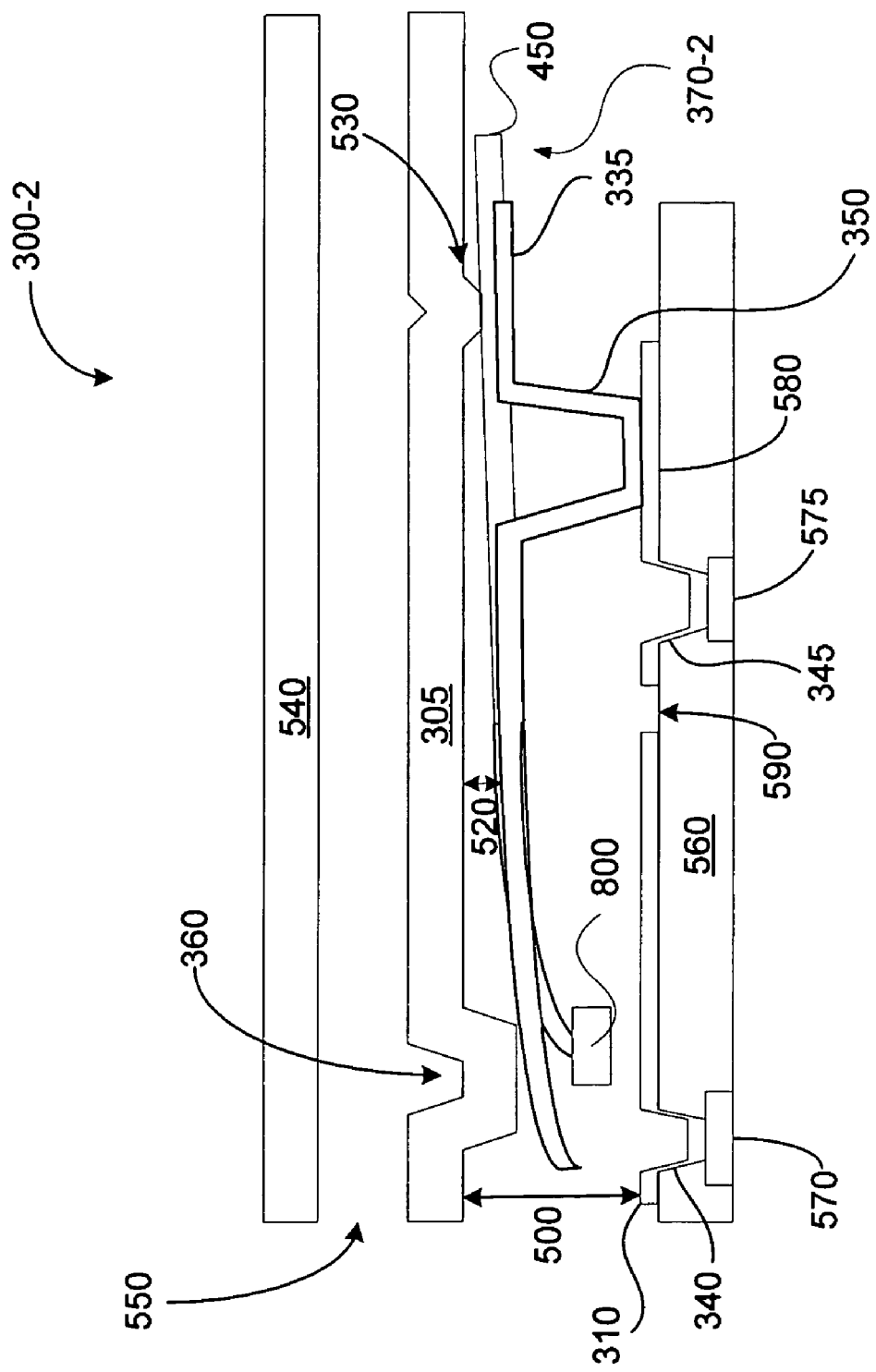

LIGHT MODULATOR DEVICE

BACKGROUND

Micro-electromechanical systems (MEMS) are used in a variety of applications such as optical display systems. Such MEMS devices have been developed using a variety of approaches. In the case of light modulator devices, the device converts white light into color light through Fabry-Perot interference between a variable height, partially reflecting pixel plate, and a fixed reflector bottom plate. The gap between the pixel plate and bottom reflector is controlled by a balance of forces between an electrostatic field and elastic deformation of pixel flexures.

The electrostatic field is produced by a voltage or charge difference between the conductive pixel plate and the conductive bottom capacitor plate. The electrostatic field pulls the pixel plate towards the bottom capacitor plate. Frequently, long, thin flexures span between fixed posts and the pixel plate. These flexures deform elastically as the pixel plate is electrostatically attracted to the bottom plate capacitor. When the voltage or charge difference between the pixel plate and bottom plate capacitor is removed, the stored elastic energy in the flexures returns the pixel plate to its original position.

To maximize the optical efficiency of the original Fabry-Perot device, the controllable pixel plate range is approximately 4000 Å. To control a pixel using traditional flexure designs, an electrostatic gap of over three times larger than the desired optical gap would be required to drive the pixel without snap-in. This large electrostatic gap results in a relatively large pixel size.

SUMMARY

A light modulator device includes a bottom charge plate, a top charge plate, and a pixel plate supported by at least one piece-wise linear flexure.

BRIEF DESCRIPTION OF THE DRAWINGS

The accompanying drawings illustrate various embodiments of the present apparatus and method and are a part of the specification. The illustrated embodiments are merely examples of the present apparatus and method and do not limit the scope of the disclosure.

FIG. 9 illustrates a side view of a light modulator device having a control gap structure including a pull-in pad during activation, according to one exemplary embodiment.

Throughout the drawings, identical reference numbers designate similar, but not necessarily identical, elements.

DETAILED DESCRIPTION

Micro-electro mechanical (MEM) light modulator devices are provided herein that have relatively large pixel plate ranges. The pixel plate range of a light modulator device is the range of translation available to a pixel plate for modulating light output. According to a number of exemplary embodiments, the light modulator devices described herein include piece-wise linear springs designs that allow the light modulator designs to have relatively small electrostatic gaps. The ability to incorporate relatively small electrostatic gaps that provide adequate pixel plate ranges may enable smaller pixel sizes by enabling a larger, controllable pixel displacement range for a given pixel size/voltage. Additionally, smaller pixel sizes may be developed resulting in lower cost devices.

As described herein, a display system will first be discussed, followed by a general discussion of an exemplary light modulator device that includes piecewise linear flexures. According to one exemplary embodiment, the piecewise linear flexures include a standard flexure having one or more control arms. Thereafter, a light modulator device will be discussed according to one exemplary embodiment, including a method of forming such a device. Thereafter, additional exemplary light modulator devices and configurations will be discussed, including light modulator devices having flexures with one or more control arms and pull-in pads.

In the following description, for purposes of explanation, numerous specific details are set forth in order to provide a thorough understanding of the present method and apparatus. It will be apparent, however, to one skilled in the art, that the present method and apparatus may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Display System

Figure 1:
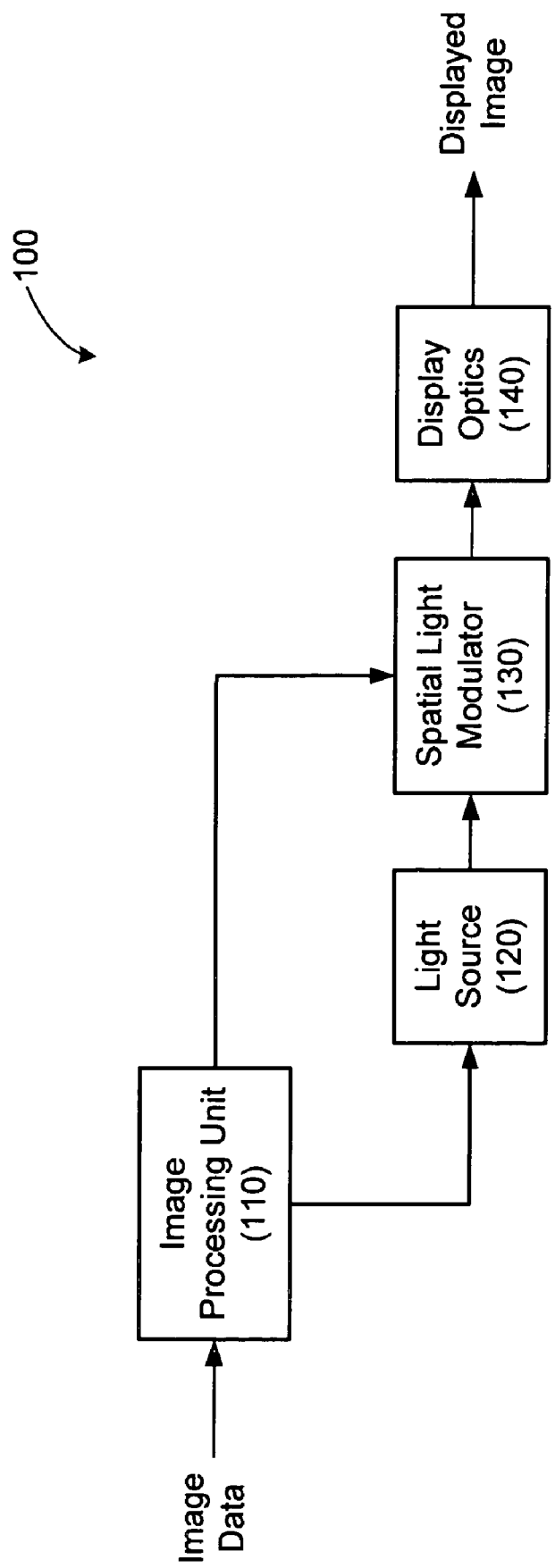
FIG. 1 illustrates a schematic diagram of a display system according to one exemplary embodiment.

FIG. 1 illustrates an exemplary display system (100). The components of FIG. 1 are exemplary only and may be modified or changed as best serves a particular application. As shown in FIG. 1, image data is input into an image processing unit (110). The image data defines an image that is to be displayed by the display system (100). While one image is illustrated and described as being processed by the image processing unit (110), it will be understood by one skilled in the art that a plurality or series of images may be processed by the image processing unit (110). The image processing unit (110) performs various functions including controlling the illumination of a light source (120) and controlling a spatial light modulator (SLM) (130). The SLM (130) will now be discussed in more detail.

The SLM (130) includes an array of micro-electro mechanical (MEM) light modulator devices, or pixels, which have optical cavities defined therein. Each optical cavity has an optical gap formed between two opposing reflectors. The size of the gap is controlled by balancing a spring force and an electrostatic force between the two reflectors. Light that enters each pixel is modulated or manipulated to achieve desired characteristics. These characteristics, which include the hues and intensities of the transmitted light, are manipulated by varying the gap between the reflectors. Further, as will be discussed in more detail below, the aperture ratio of each light modulator device is relatively large. This increase in the aperture ratio of each light modulator device increases the amount of light transmitted by each light modulator.

Returning to the operation of the display system (100) in general, the SLM (130) manipulates incoming light to form an image-bearing beam of light that is eventually displayed or cast by display optics (140) on a viewing surface (not shown). The display optics (140) may comprise any device configured to display or project an image. For example, the display optics (140) may be, but are not limited to, a lens configured to project and focus an image onto a viewing surface. The viewing surface may be, but is not limited to, a screen, a television, a wall, a liquid crystal display (LCD), or a computer monitor. The pixel structures described herein allow the size of the reflectors to be precisely controlled while minimizing or eliminating undesired contact between the two reflectors and/or other parts of the pixel. This control also includes the control of the black state of the pixel.

Light Modulator Device having Separate Optical and Electrostatic Gaps

Figure 2:
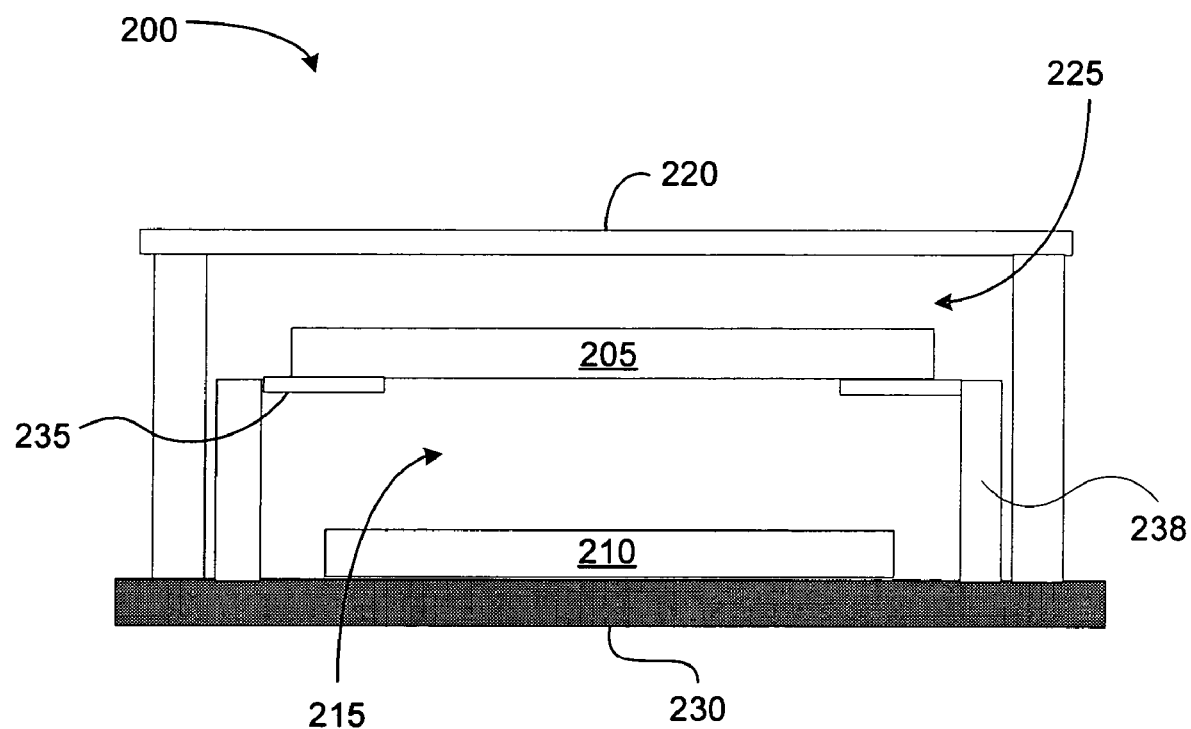
FIG. 2 illustrates a schematic diagram showing a hide control gap pixel structure according to one exemplary embodiment.

FIG. 2 illustrates the operation of a single light modulator device. The light modulator device (200) includes a pixel plate (205) and a bottom charge plate (210) separated by an electrostatic gap (215). The light modulator device (200) also includes a top plate (220) that is separated from the pixel plate (205) by an optical gap (225). As will be discussed in more detail below, the pixel plate (205) occupies a relatively large percentage of the total top surface area of the light modulator device (200). For ease of reference, the surface area of the light modulator device will be discussed with reference to the surface area of the light modulator as viewed from above.

The light modulator device (200) is supported by a substrate (230). For example, a pixel support structure supports the pixel plate (205) and an outside support structure supports the top plate (220). The exemplary pixel support structure illustrated in FIG. 2 includes a plurality of fixed posts (238) and pixel extension members or flexures (235). As illustrated, the flexures (235) are located substantially below the pixel plate (205), allowing for an increase in the relative size of the pixel plate (205). In particular, the location of the flexures (235) substantially below the pixel plate (205) reduces or eliminates occlusion of the surface area of the light modulator device (200) by flexures.

The light modulator device (200) shown functions as a Fabry-Perot light modulator. As a result, the pixel plate (205) is highly reflective while the top plate (220) is less reflective. A portion of a beam of light incident on the light modulator device (200) will be partially reflected by the top plate (220), while another portion of the beam of light will pass through the top plate (220) and into the optical gap (225).

Once the light enters the optical gap (225), it is bounced between the top plate (220) and the pixel plate (205). Each time the light inside the optical gap (225) becomes incident on the top plate (220), some portion of the light passes through the top plate (220) and escapes the light modulator device (200). The wavelengths of the light that are thus able to pass through the top plate (220) depend at least in part on the size of the optical gap (225). Accordingly, varying the size of the optical gap (225) controls the characteristics of light that exits the light modulator device (200).

The size of the optical gap (225) is controlled by movement of the pixel plate (205). The optical gap (225) of the light modulator device may be precisely controlled over a broad range of displacements, or an operating displacement range, while minimizing or eliminating contact between the pixel plate (205) and the bottom charge plate (210). This operational displacement range includes movement from a position to produce a black state response through positions for producing light of selected wavelengths within the visible spectrum.

As previously introduced, controlling the size of the optical gap (225) controls the output of the light modulator device (200). Further, as previously discussed, the size of the optical gap (225) shown depends, at least in part, on the size of the electrostatic gap (215). Separating the optical gap (225) and the electrostatic gap (215) as illustrated in FIG. 2 allows for flexibility and device performance enhancements in the light modulator devices. Specifically, this configuration allows for increased degrees of freedom in the flexure design and for a higher aperture ratio. According to one exemplary embodiment, the aperture ratio of the present exemplary device may be, but is in no way limited to, 0.75 or 0.85, increasing the optical performance of the light modulator device (200).

Storing electrical charge on the pixel plate (205) and/or the bottom charge plate (210) varies the size of the optical gap (225), such that a desired wavelength at a desired intensity may be selected. The flexures (235) allow the electrostatic gap (215) to vary when charge is stored on the pixel plate (205) and the bottom charge plate (205). The charge stored results in an electrostatic force between the plates (205, 210), thereby drawing the pixel plate (205) toward the bottom charge plate (210). This force is opposed by the spring force associated with the deflection of the flexures (235) and the control arm, as will be described in further detail below.

When an electrostatic force exists between the pixel plate (205) and the bottom charge plate (210), the pixel plate will continue to be drawn toward the bottom charge plate until the spring force and the electrostatic force reach equilibrium. When these two forces reach equilibrium, the pixel plate (205) will be held in a substantially constant position. Accordingly, the relative position of the pixel plate (205) with respect to the bottom charge plate (210) and the top plate (220) may be varied by the amount of charge applied to the plates (205, 210). Once the electrostatic force is released, such as by dissipating the accumulated charges, the spring force returns the flexures (235) to a neutral state position.

Traditionally, the total initial electrostatic gap (215), which is the total distance between the pixel plate (205) and the bottom charge plate (210) while the pixel plate (205) is un-deflected, was sized to reduce the possibility that the pixel plate (205) will come into contact with the bottom charge plate (210). More specifically, as mentioned previously, traditional light modulator devices incorporated an electrostatic gap (215) that was over three times as large as the desired optical gap (225) to prevent undesirable conditions such as snap-in. Snap-in occurs when the pixel plate (205) and the bottom charge plate (210) are charged such that they are drawn together by electrostatic forces that overcome the spring force exerted by the flexures (235). Often the snap-in condition is a result of charge runaway.

While the traditional incorporation of the large initial electrostatic gap (215) helped to reduce the occurrence of snap-in, the large initial electrostatic gap also increased the overall size and cost of traditional light modulator devices (200). Consequently, the exemplary light modulator devices (200)

described herein include bi-modal flexures that reduce the likelihood of snap-in while reducing the electrostatic gaps (215).

Accordingly, several exemplary structures will be discussed herein that include bi-modal flexures that are placed substantially below the pixel plate (205). An exemplary light modulator device will also be discussed that makes use of the bi-modal flexures. The exemplary pixel plate, bi-modal flexures, and their associated control arms will then be discussed in more detail with reference to FIGS. 4 and 5. As will be discussed in more detail below, the separation of the optical gap and the electrostatic gap may further allow for more efficient formation of electrical connections. An exemplary method of forming of a light modulator device will then be discussed with reference to FIG. 6. Several other configurations will then be discussed with reference to FIGS. 7-9.

Exemplary Light Modulator Device

Figure 3:
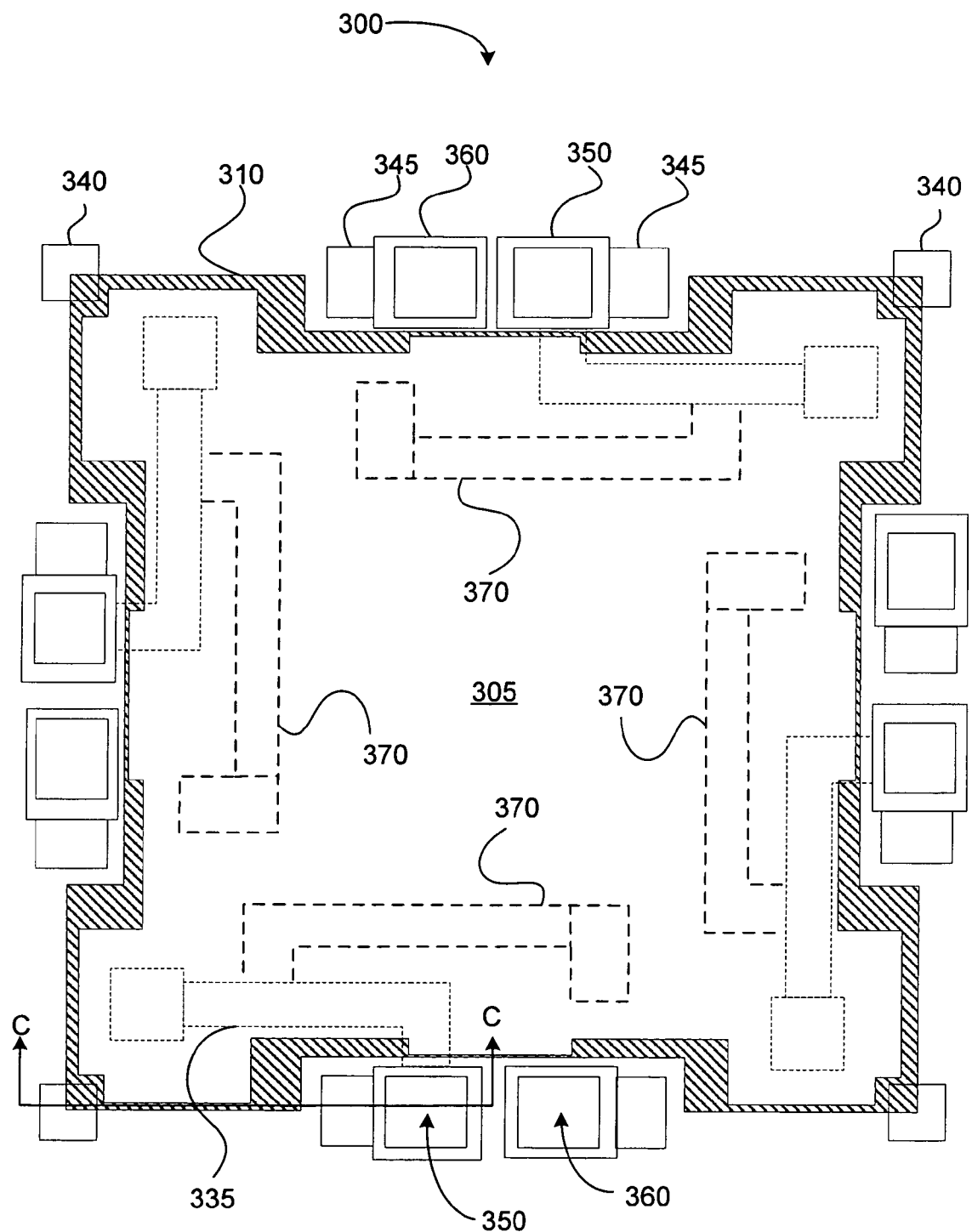
FIG. 3 illustrates a partial top view of a light modulator device having a control gap flexure structure, according to one exemplary embodiment.

FIG. 3 illustrates a top view of a light modulator device (300). For ease of reference, the top charge plate has been removed, but will be discussed in more detail with reference to FIGS. 5 and 6. The light modulator device (300) illustrated in FIG. 3 includes a plurality of flexures (335) that extend from posts between the bottom charge plate (310) and the pixel plate (305). These flexures (335), which are arranged in a pinwheel pattern, are shown in dashed lines to emphasize that a substantial portion of the flexures (335) is located below the pixel plate (305). Accordingly, as shown in FIG. 3, the ratio of the surface area of the pixel plate to the total surface area of the light modulator to the device is relatively high.

Additionally, as illustrated in FIG. 3, a number of control arms (370) are coupled to the illustrated flexures (335). As shown, the control arms (370) are also located below the pixel plate (305), and protrude from the flexures (335). According to one exemplary embodiment, the control arms (370) are not in direct contact with or coupled to the pixel plate (305) when in an un-deflected state. However, as the above-mentioned electrostatic attraction between the bottom charge plate (310) and the pixel plate (305) is generated and the electrostatic gap (215; FIG. 2) is reduced, the control arms (370) may contact the pixel plate (305) and provide increased resistance to further translation, as will be described in further detail below with reference to FIGS. 4 and 5A-B.

The pixel plate (310) and flexures (335) will now be discussed in more detail with reference to FIGS. 4, 5A and 5B. By way of introduction, the light modulator device (300) includes a plurality of bottom plate vias (340), interconnect vias (345), flexure vias (350), and pixel plate vias (360) that facilitate the generation of electrostatic attraction between the components of the light modulator device (300), according to one exemplary embodiment. The configuration of the vias will be discussed in more detail with reference to FIG. 6.

Figure 4:
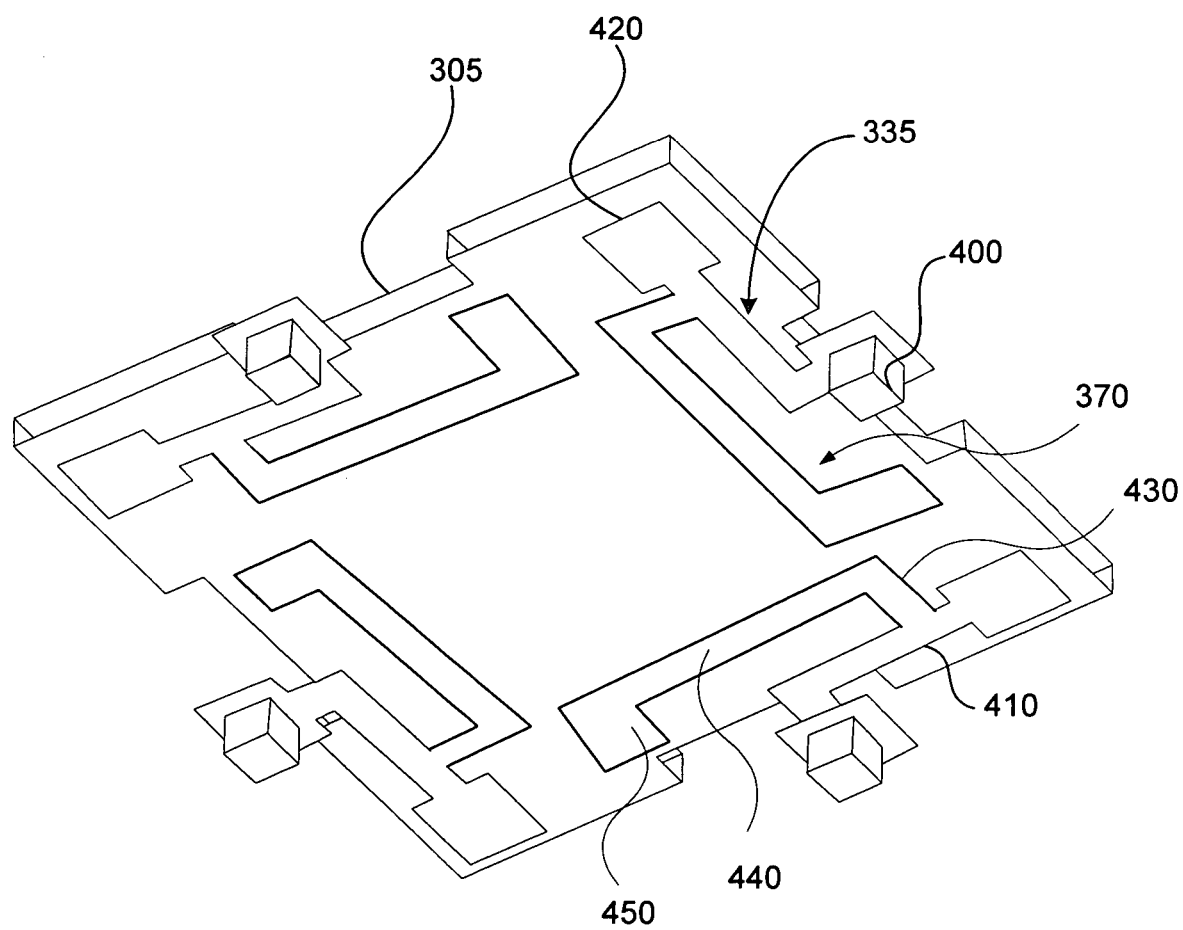
FIG. 4 illustrates a bottom perspective view of a pixel plate and exemplary flexures, control arms, and posts, according to one exemplary embodiment.

FIG. 4 illustrates a bottom view of the pixel plate (305), the flexures (335), and the control arms (370) isolated from the other components of the light modulator device (300). As shown in FIG. 4, the flexures (335) are coupled to a base mounting post (400), and include a span portion (410), and a pixel plate mounting portion (420). The base mounting portion (400) of the flexures (335) is secured to the interconnect vias (345; FIG. 3), and the pixel plate mounting portion (420) is secured to the pixel plate (305). The span portion (410) shown is approximately 5.4 μm in length by approximately 1.0 μm wide, according to one exemplary embodiment. This configuration allows the span portion (410) to deflect in response to the electrostatic forces discussed above. As the span portion (410) deflects, the amount of the space between the pixel plate (305) and the bottom charge plate (310; FIG. 3) changes.

Additionally, as illustrated in the exemplary embodiment of FIG. 4, a control arm (370) protrudes from each of the flexures (335) at a control arm axis (430) located at or near a center point between where the flexure is attached to the base mounting post (400) and the pixel plate mounting portion (420). While the present exemplary light modulator device (300; FIG. 3) is described as having a control arm (370) protruding from each flexure (335), any number of control arms (370) may be associated with the flexures to provide a piece-wise linear spring. Continuing with FIG. 4, the control arm (370) includes a control arm axis (430) that is coupled to the span portion (410) of the flexures (335). A control arm span (440) is disposed in substantially the same plane as its associated flexure (335) and is oriented in a substantially tangential direction to the control arm axis (430) extending in a direction opposite of the pixel plate mounting portion (420) of the associated flexure (335). At the termination of the control arm span (440), opposite the control arm axis (430), a pixel plate contact (450) is formed. According to one exemplary embodiment, the pixel plate contact (450) is configured to contact and provide increased resistance to the pixel plate (305) upon flexure of the associated flexure (335) as will be discussed in further detail below with respect to FIGS. 5A and 5B.

Figure 5A:
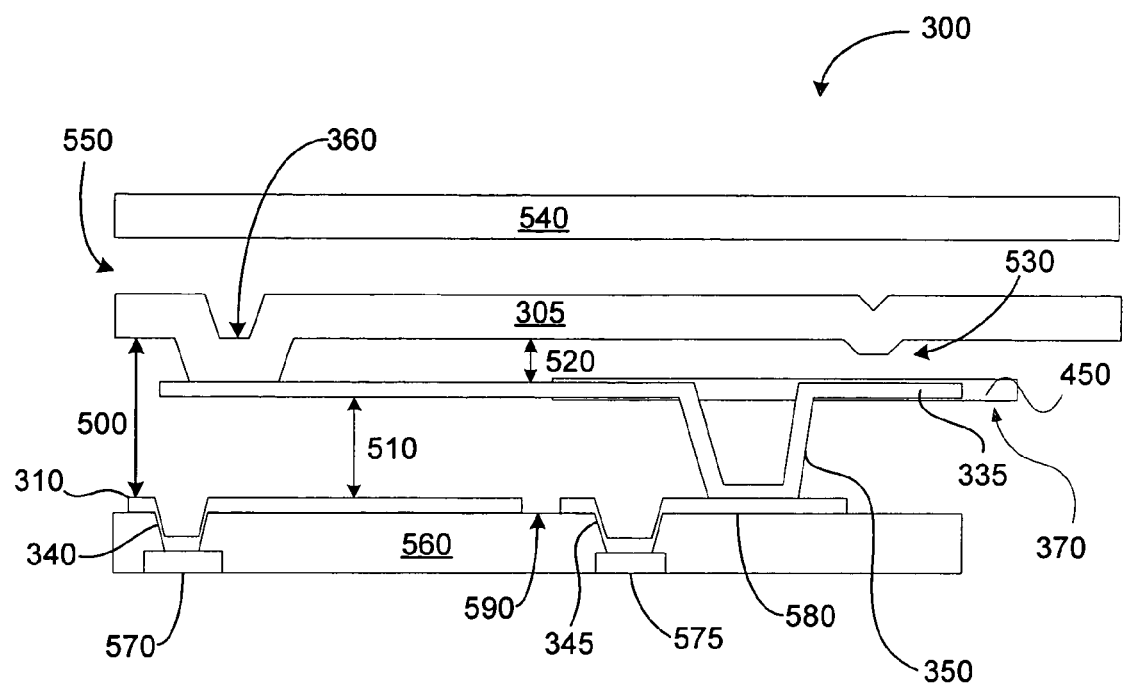
FIG. 5A illustrates a partial cutaway view of a light modulator device, according to one exemplary embodiment.
Figure 5B:
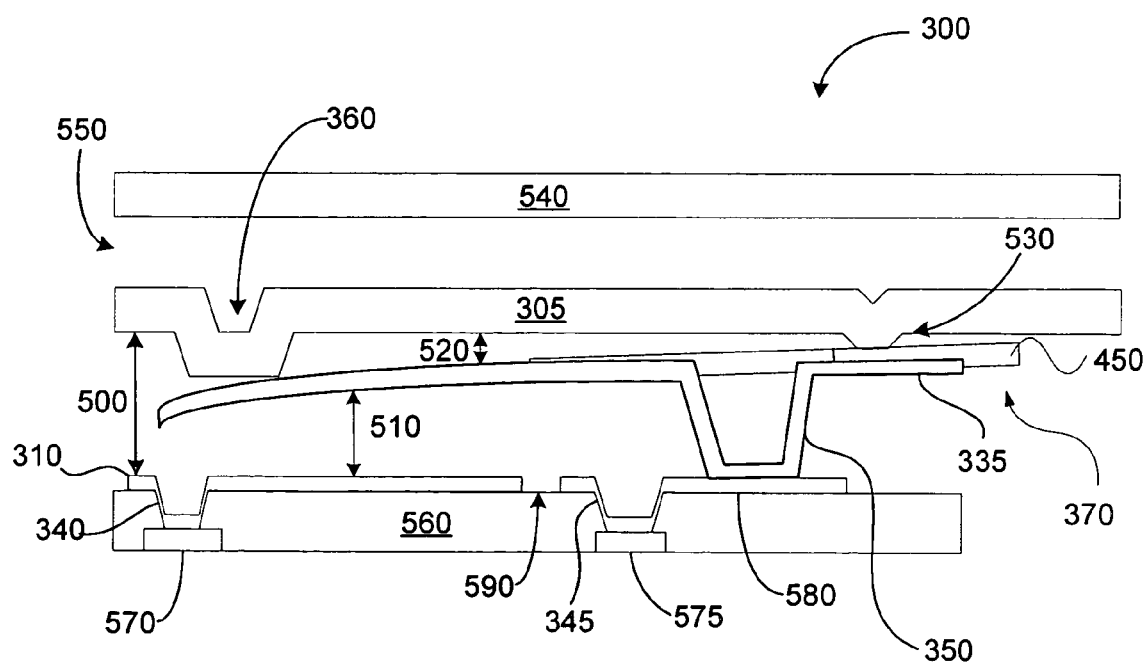
FIG. 5B illustrates a partial cutaway view of a light modulator device in an actuated state, according to one exemplary embodiment.

FIG. 5A is a partial cutaway side view of an exemplary light modulator device (300) incorporating a piece-wise linear spring including a control arm (370) in an un-deflected or neutral state taken along section C-C. As shown in FIG. 5A, an electrostatic gap (500) is defined between the pixel plate (305) and the bottom charge plate (310). This electrostatic gap (500) includes a first sacrificial layer space (510) between the flexures (335) and the bottom charge plate (310) and a flexure space (520) between the pixel plate (305) and the flexure (335). Additionally, an optical gap (550) is defined between the top charge plate (540) and the pixel plate (305).

The neutral state position of the pixel plate (305) illustrated in FIG. 5A corresponds to the black state position of the pixel plate (305) such that the optical gap (550) in this configuration is at its minimum size. According to one exemplary embodiment, the optical gap (550), which is defined between the top charge plate (540) and the pixel plate (305), is approximately 100 nm when in the black state position. This electrostatic gap allows the light modulator device (300) to absorb sufficient light to be in a black state. More specifically, the size of the optical gap (550) while the pixel plate (305) is in a black state position allows the light modulator device (300) to trap essentially all of the light that enters therein, such that the light modulator device produces a black output. As introduced, the light modulator device (300) may be reliably placed in its black state position by allowing the pixel plate (305) to return to its neutral state position.

During operation, electrostatic charges are established on each of the pixel plate (305) and the bottom charge plate (310) to thereby controllably draw the pixel plate (305) toward the bottom charge plate (310). Additionally, the top charge plate (540) may be coupled to the same voltage level as the pixel plate (305) such that there is little or no electrostatic attraction between the top charge plate (540) and the pixel plate (305). Alternatively, the top charge plate (540) may be replaced by a completely non-conductive plate that generates little or no electrostatic attraction with the pixel plate (305).

As the pixel plate (305) is drawn toward the bottom charge plate (310), both the first sacrificial space (510) and the flexure space (520) become smaller. These spaces will continue to become smaller until the pixel plate (305) contacts the flexure (335), the flexure (335) contacts the bottom charge plate (310), and/or the flexure resistance is equal to or greater than the attractive force.

As previously introduced, the light modulator device (300) includes a plurality of bottom plate vias (340), interconnect vias (345), flexure vias (350), and pixel plate vias (360) configured to generate the above-mentioned electrostatic charges. According to one exemplary embodiment, the bottom charge plate (310) is electrically coupled to a first source connection (570) through the bottom plate via (340), as illustrated in FIG. 5A. Additionally, the pixel plate (305) is electrically coupled to a second source connection (575) through pixel vias (360), flexure vias (350) and interconnect vias (345). Both the first source connection (570) and the second source connection (575) are configured to be coupled to external voltage sources to controllably provide voltage to the bottom charge plate (310) and the pixel plate (305), respectively.

In the exemplary embodiment of FIG. 5A, the flexure space (520) is smaller than the first sacrificial space (510). As a result, the pixel plate (305) will contact the flexure (335) before the flexure (335) contacts the bottom charge plate (310), thereby reducing charge trapping and arc welding stiction mechanisms. Additionally, the effects may be further reduced by including a bump (530) between the flexure (335) and the pixel plate (305). In particular, in such a configuration the bump (530) is formed on the underside of the pixel plate (305). A plurality of such bumps may be located over each of the base mounting posts (400; FIG. 4) to reduce stiction mechanisms.

As previously discussed, continued performance of the light modulator device (300) depends, at least in part, on the ability of the flexures (335) to resist snap-in conditions during electrostatic displacement of the pixel plate (305). The incorporation of the control arms (370) coupled to the flexures (335) create a piece-wise linear spring that resists snap-in while incorporating a reduced electrostatic gap (215; FIG. 2).

More specifically, according to one exemplary embodiment, the initial resistance to an electrostatic attraction to the bottom charge plate (210) by the pixel plate (205) is provided by the flexures (335), which are fixedly coupled to the pixel plate at the pixel plate mounting portion (420; FIG. 4). As the pixel plate (305) is electrostatically attracted to the bottom charge plate (310), the translation of the pixel plate will be resisted by the span portion (410; FIG. 4) of the flexure.

However, as the electrostatic gap (500) is reduced due to translation of the pixel plate (305), the electrostatic attraction between the pixel plate and the bottom charge plate (310) increases, thereby increasing the likelihood of a snap-in condition. However, as illustrated in FIG. 5B, continued translation of the pixel plate (305) due to an electrostatic attraction to the bottom charge plate (310) will meet increased resistance due to the control arm (370). More specifically, as illustrated in FIG. 5B, deflection in a downward direction by the flexure (335) will cause the pixel plate contact (450) of the control arm (370) to move in an upward direction towards the pixel plate (305). Because the control arm axis (430; FIG. 4) is coupled to the span portion (410; FIG. 4) of the associated flexure (335), and due to the control arm span (440; FIG. 4) of the control arm (370) being oriented in a direction opposite the flexure, motion in a negative or downward direction by the pixel plate mounting portion (420; FIG. 4) of the flexure will cause a movement in the positive direction of the pixel plate contact (450). When the pixel plate (305) has been deflected to a predetermined point, the pixel plate contact (450) will contact the pixel plate (305), as illustrated in FIG. 5B.

Once the control arm (370) has contacted the pixel plate (305), further translation of the pixel plate (305) due to electrostatic attraction to the bottom charge plate (310) will be resisted by deformation of both the flexure (335) and the control arm (370). Consequently, this piece-wise linear resistance provided by the exemplary embodiment illustrated in FIG. 3B resists snap-in conditions and allows for the construction and use of light modulator devices (300) incorporating smaller electrostatic gaps (500).

The point at which the pixel plate contact (450) contacts the pixel plate (305) may be varied by varying the length of the control arm span (440; FIG. 4). More specifically, an increase in the control arm span (440; FIG. 4) will amplify the translation of the pixel plate contact (450) in response to a bending of the flexure (335). Similarly, a reduction in the control arm span (440; FIG. 4) will reduce the sensitivity of the pixel plate contact to a bend in the flexure (335). Further, the contact point of the pixel plate contact (450) may be varied by the formation of a bump (530) as illustrated in FIGS. 5A and 5B. More specifically, by varying the height of the bump (530) formed in the pixel plate (305), the amount of translation sufficient to cause contact with the pixel plate contact (450) may be modified.

Method of Forming a Light Modulator Device

Figure 6A:
FIGS. 6A-6Q illustrate a method of forming a control gap light modulator, according to one exemplary embodiment.
Figure 6B:
Figure 6C:
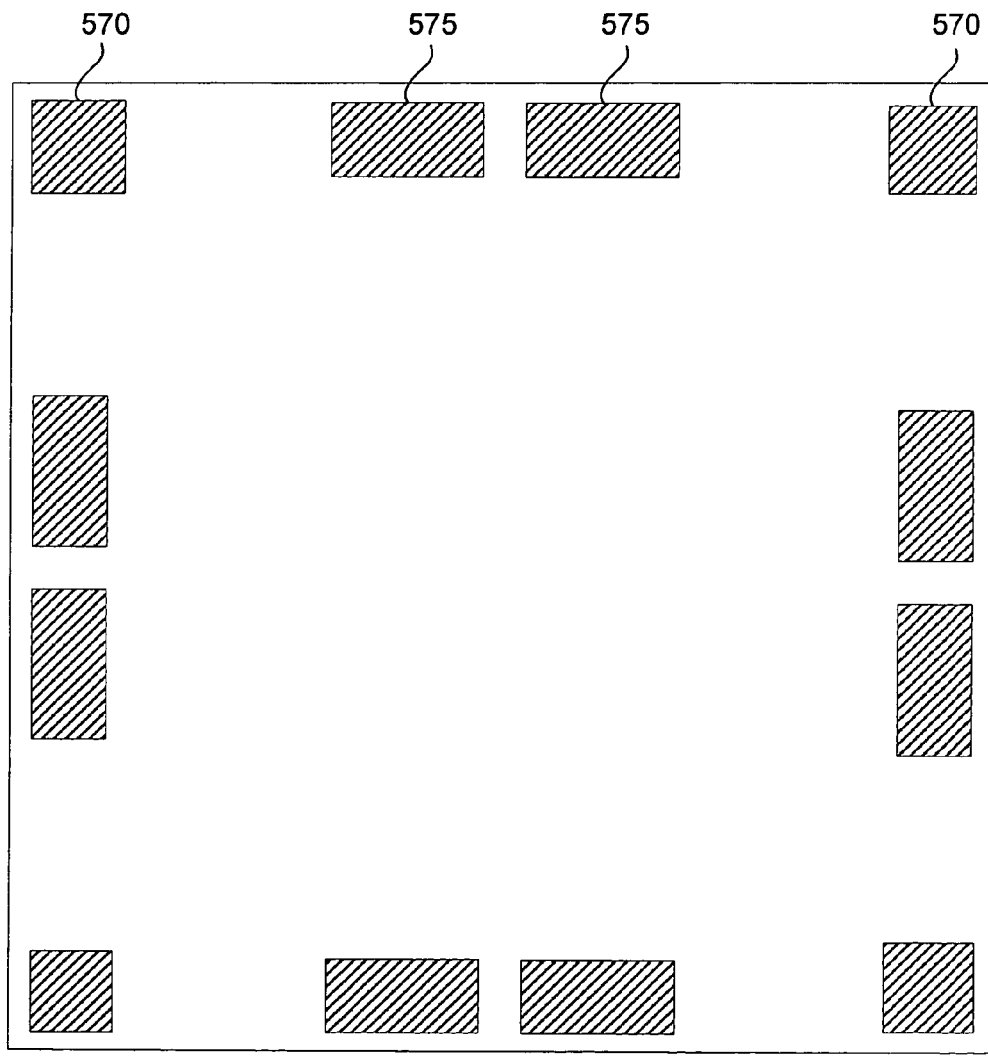
Figure 6D:
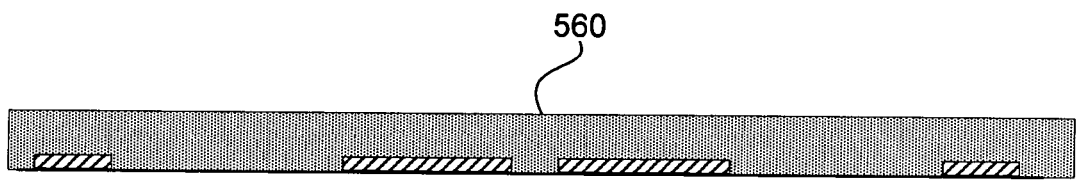
Figure 6E:
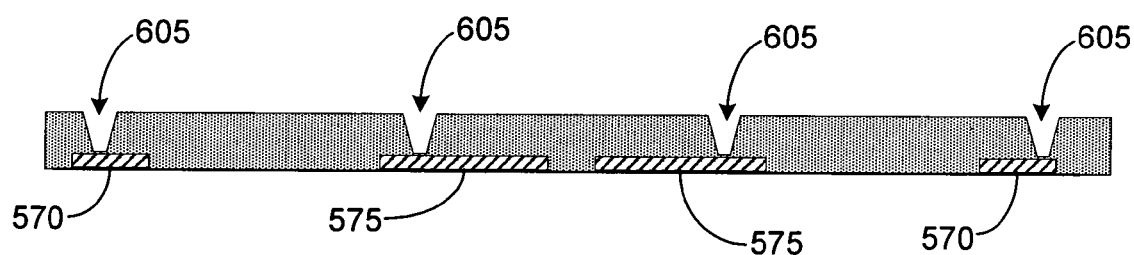
Figure 6F:
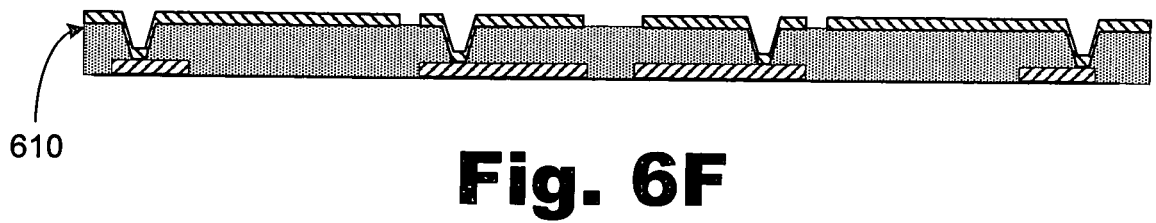
Figure 6G:
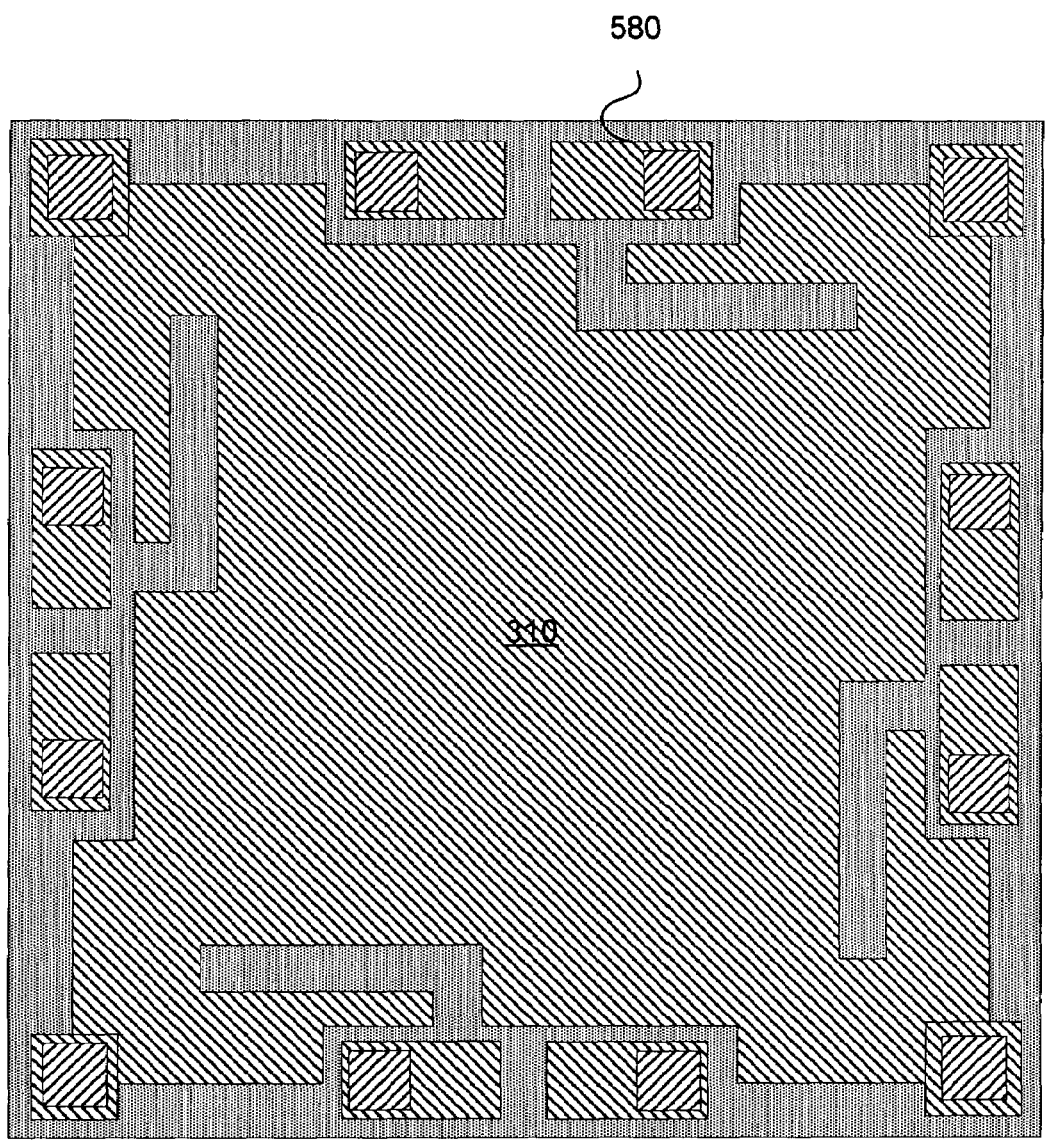
Figure 6H:
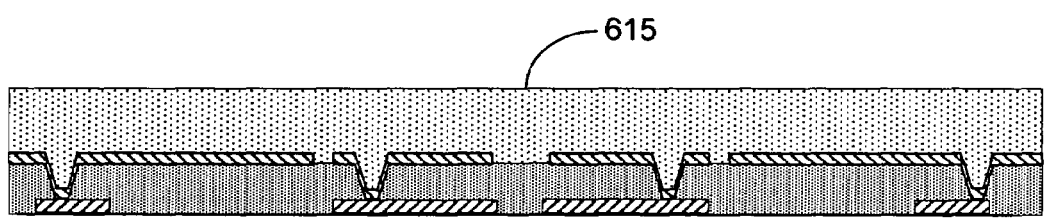
Figure 6I:
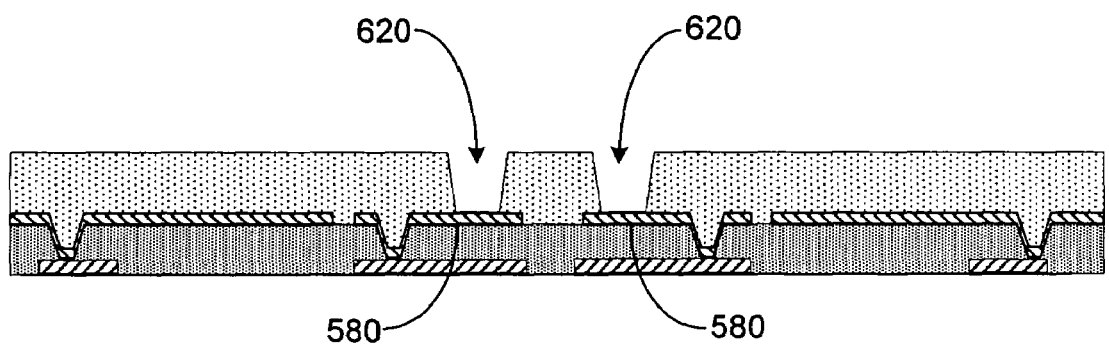
Figure 6J:
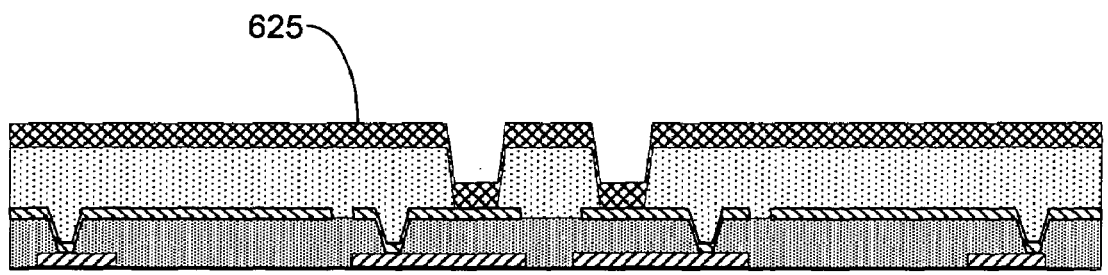
Figure 6K:
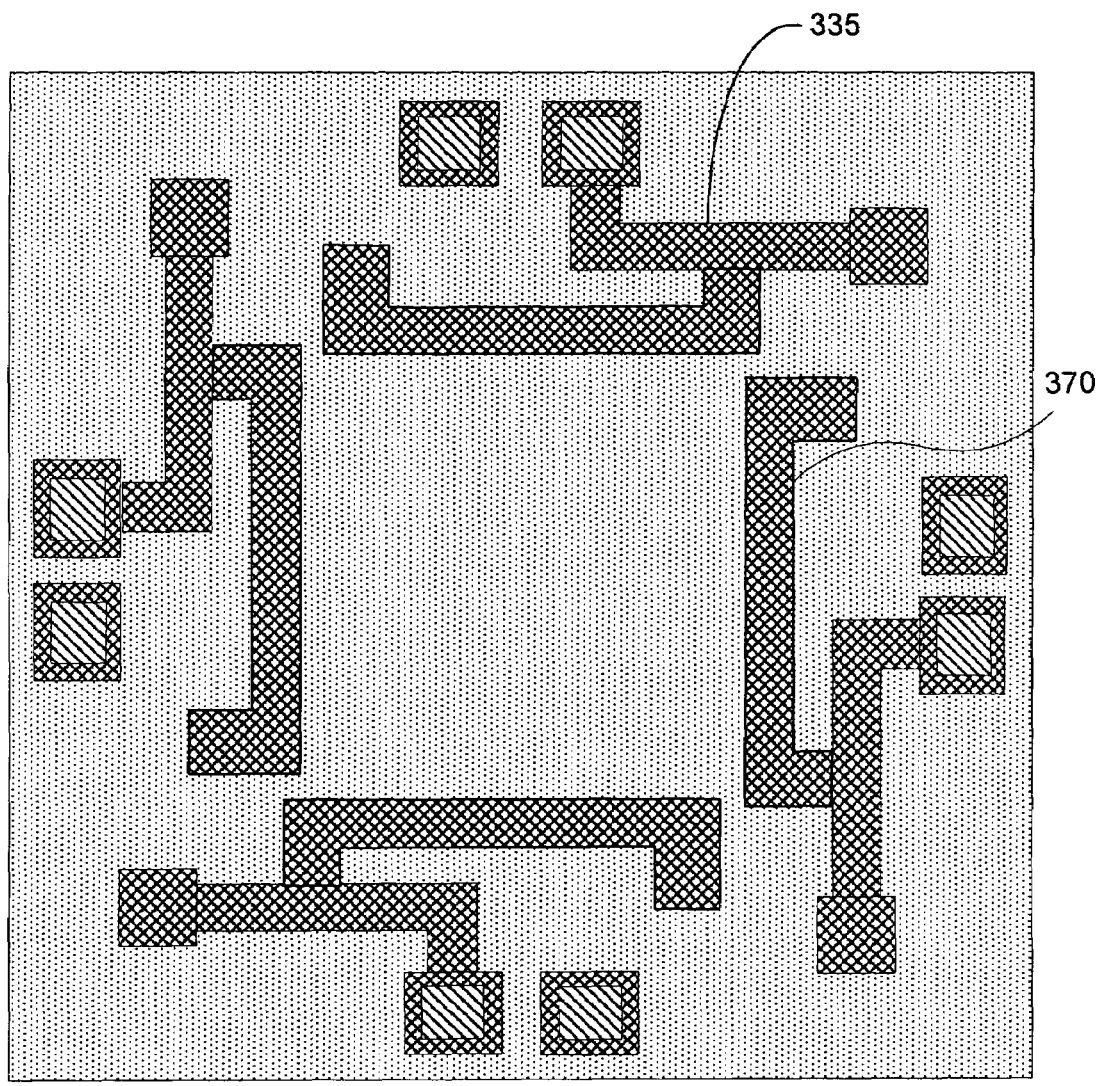
Figure 6L:
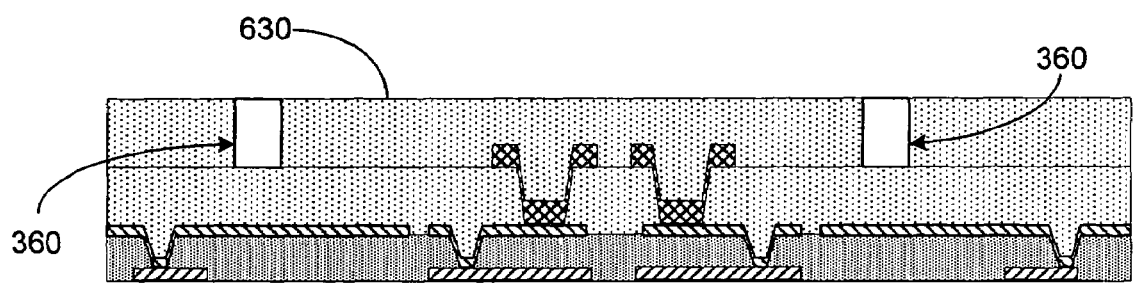
Figure 6M:
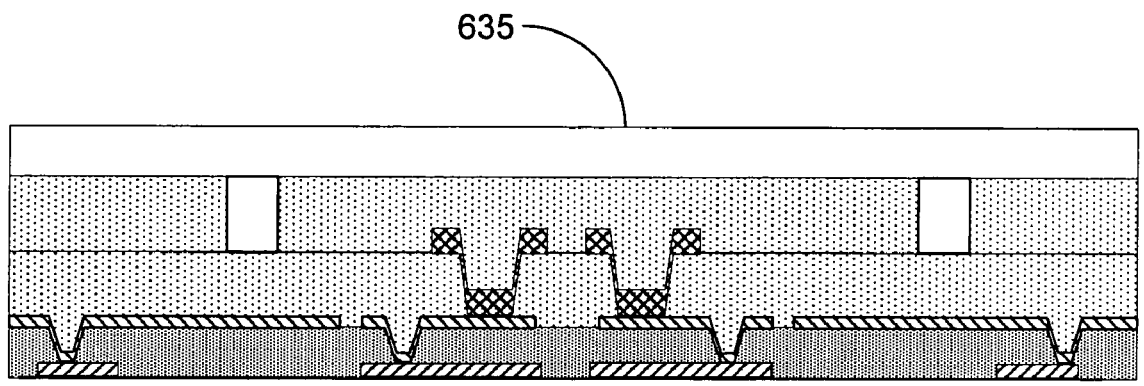
Figure 6N:
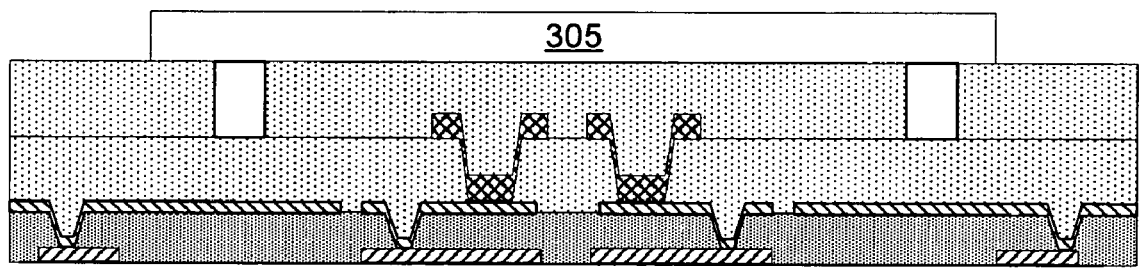
Figure 6O:
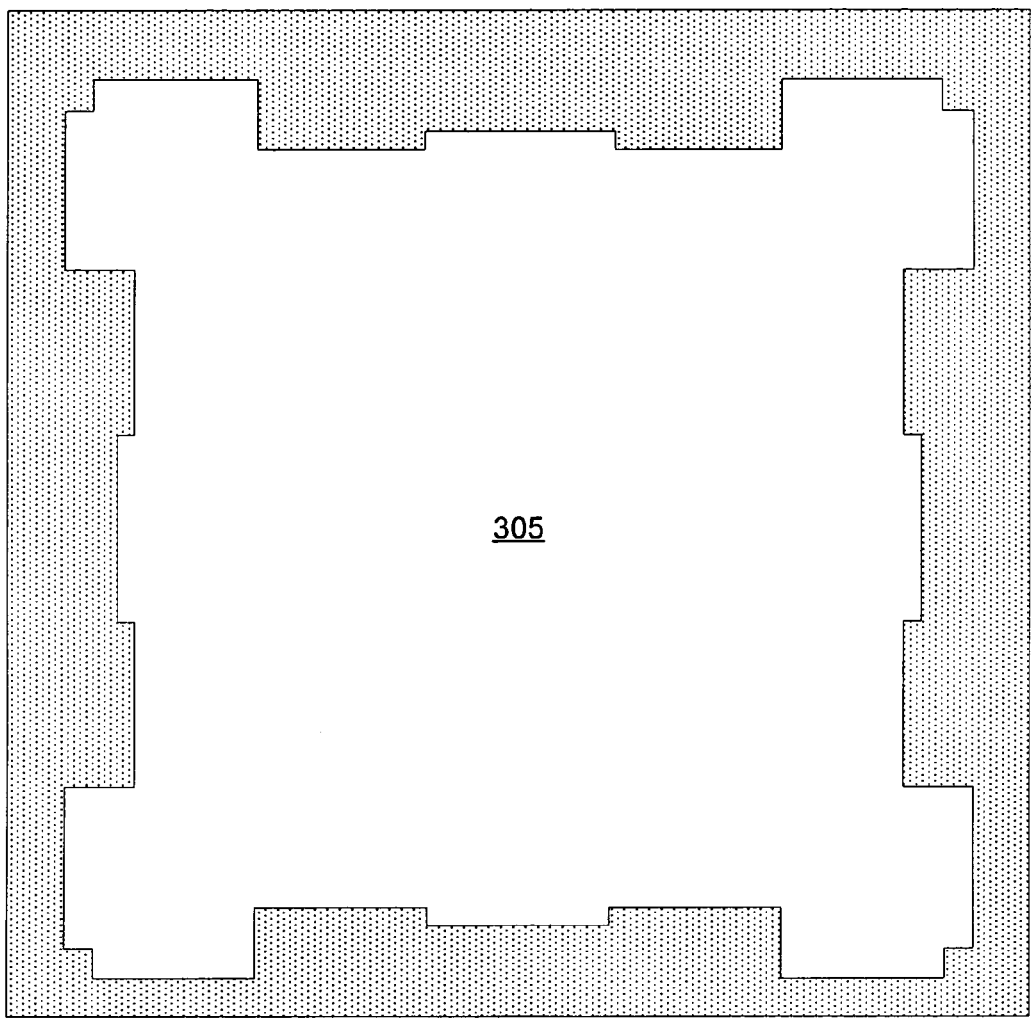
Figure 6P:
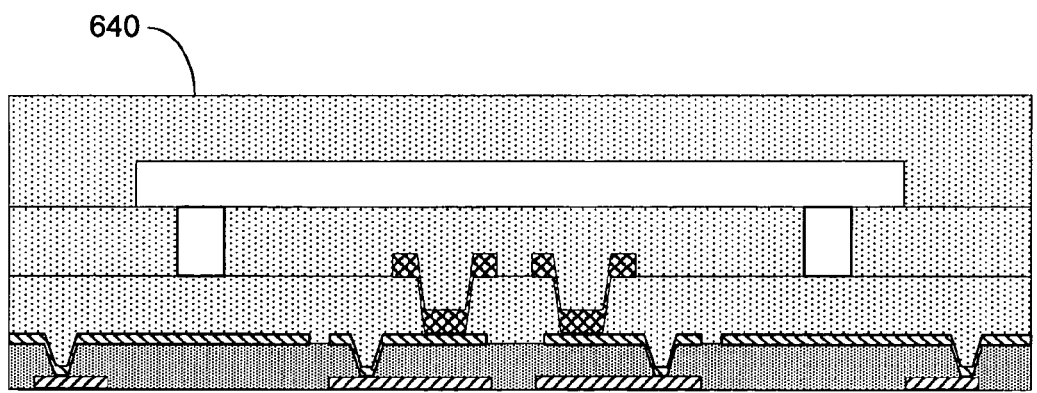
Figure 6Q:
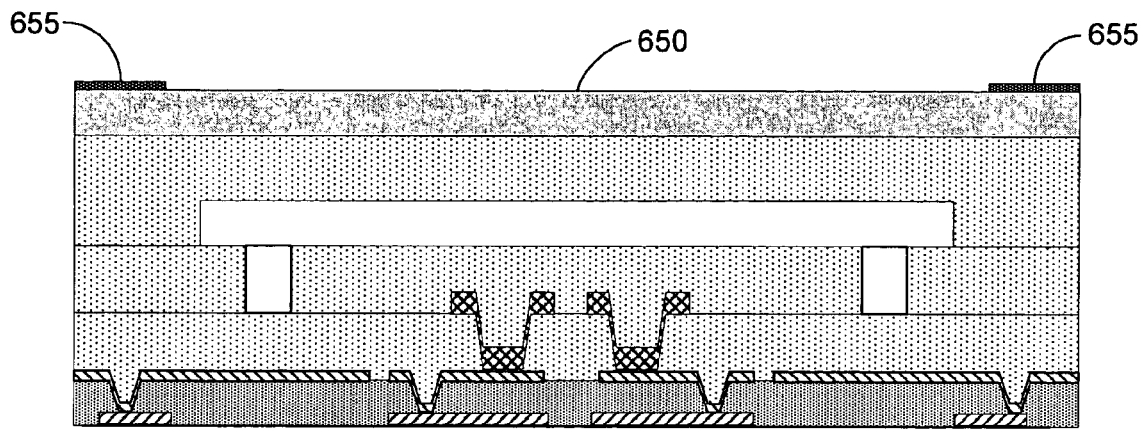

FIGS. 6A-6Q illustrate an exemplary method of forming a light modulator device. For ease of reference, the method will be discussed with respect to the formation and processing of layers of material. As shown in FIG. 6A, the method begins by forming a source connection layer (600). One such exemplary layer includes 50 Å Ti, 500 Å of TiN, and 1500 Å of AlCu on a substrate. Thereafter, the layer of metal material is processed to form the source connections (570, 575; FIGS. 6B-C). The source connection layer (600) is processed by applying a source connection photoresist pattern that corresponds to the final shapes of the source connections. The source connection layer is then etched to remove excess material, thereby leaving the finished bottom source connections (570, 575).

A bottom oxide layer (560), such as a TEOS layer, is formed on the remaining source connection layer, as is shown in FIG. 6D. One exemplary bottom oxide layer is approximately 1 μm thick. As shown in FIG. 6E, the bottom oxide layer (560) is then processed to form via pathways (605) that extend through the bottom oxide layer (560) and to the source connections (570, 575). In particular, a first via photoresist pattern is applied to the first bottom oxide layer (560) and the exposed areas are then etched through to the source connection layer. The exposed areas of the first via photoresist pattern correspond to the size, shape, and locations of the vias. These via pathways correspond to the first or bottom source vias and the interconnect vias, which are formed above the first metal source connections (570) and the second metal source connections (575) respectively.

FIGS. 6F and 6G illustrate the device after a bottom charge plate layer (610) has been deposited and etched. The deposition of the bottom charge plate layer causes a layer of material to be deposited in the via pathways (605; FIG. 6E), which are formed through the bottom oxide layer (560; FIG. 6D). Accordingly, an electrical connection is established between the source connection layer and the bottom charge plate layer by way of the vias. The bottom charge plate layer is then processed to form the bottom charge plate shown in FIGS. 6F-6G. This processing may include applying a bottom charge plate photoresist pattern and etching through the exposed areas to the bottom oxide layer (560). As the bottom charge plate layer is etched, the bottom charge plate (310) and the intermediate charge plate (580) are established in the bottom charge plate layer (610).

A first sacrificial layer (615; FIG. 6H) is then formed on the bottom charge plate layer (610). One exemplary first sacrificial layer (615; FIG. 6H) includes a 200 Å layer of SiN and a 3300 Å layer of a-Silicon. As shown in FIG. 6I, the first sacrificial layer (615; FIG. 6H) is then processed to form pathways (620) for flex plate via applying a flex plate via photoresist pattern to the first sacrificial layer and then etching through the first sacrificial layer (620) to the intermediate charge plates (580), which are part of the bottom charge plate layer (610; FIG. 6F).

As previously introduced, the flexures (335; FIG. 5) may include bumps (530-1; FIG. 5B) on the underside thereof. These bumps may be formed by forming voids or molds in the first sacrificial layer (615). These voids may be formed by applying a bump void photoresist pattern to the first sacrificial layer. A suitable bump void photoresist pattern may have voids therein corresponding to the size, shape, and location of the individual voids to be formed in the first sacrificial layer. The first sacrificial layer (615) would then be etched to a depth of approximately 500-1000 Å to form the voids. Accordingly, the first sacrificial layer may be processed to provide bumps on the underside of the flexures.

FIG. 6J shows the flexure and control arm layer (625). According to one exemplary embodiment, the flexure and control arm layer (625) is approximately 1200 Å thick and is substantially made up of TaAl. The flexure and control arm layer (625) is processed by applying a flexure photoresist pattern to the flexure and control arm layer (625) and etching through to the first sacrificial layer (615; FIG. 6H). The resulting flexure pattern, including the flexures (335) and their associated control arms (370), is shown in FIG. 6K. Alternative to the exemplary embodiment illustrated above, the flexure and control arm layer (625) may be formed out of any number of appropriate materials including, but in no way limited to, a metallic material such as aluminum or silver, an oxide layer, and/or a nitride layer.

A flexure space sacrificial layer (630) is then deposited on the flexure and control arm layer (625; FIGS. 6J-6K), as is shown in FIG. 6L. The flexure space sacrificial layer (630), according to one exemplary embodiment, includes approximately 3300 Å a-Si and 200 Å SiN material. The flexure space sacrificial layer (630) corresponds to the flexure space (520) shown in FIGS. 5A-5B. Pixel vias (360) are then etched into the flexure space sacrificial layer (630) to connect the pixel plate to the flexure. Accordingly, voids may be established in the flexure space sacrificial layer (630) for the formation of bumps (335; FIG. 5B) as previously described.

As seen in FIG. 6M, a pixel plate layer (635) is then formed on the flexure space sacrificial layer (630). According to one exemplary embodiment, the pixel plate layer is approximately 10,000 Å thick and is substantially made up of AlCu. After the pixel plate layer (635) is deposited, it is processed by applying a pixel plate photoresist pattern thereto an etching through to the flexure space sacrificial layer (630). The resulting pixel plate (305) is shown in FIGS. 6N and 6O.

Once the pixel plate (305) has been formed, a second sacrificial layer (640; FIG. 6P) is formed on the pixel plate layer (635). One second sacrificial layer includes a layer of SiN that is approximately 200 Å thick and a layer of a-Si that is approximately 2800 Å thick. Thereafter, a top charge plate layer (650) is formed on the second sacrificial layer (635), as shown in FIG. 6P. Once this structure has been formed, the first sacrificial layer (615), the flexure space sacrificial layer (630), and the second sacrificial layer (640) may be removed, such as by selective etching. A third electrical connection (655) is then formed on top of the top charge plate (640) and coupled to a third voltage source (not shown).

The top charge plate (650) and the pixel plate (305) may be coupled to the same voltage source or sources at the same voltage level. In such a case, there is little or no voltage difference between the top charge plate (650) and the pixel plate (305) such that little or no electrostatic attraction exists between the top charge plate (650) and the pixel plate (305). Further, the top charge plate (650) and the pixel plate (305) may be coupled to voltage sources at different voltage levels, such that an electrostatic attraction may be established between the top charge plate (650) and the pixel plate (305).

Accordingly, the present method provides for the formation of a light modulator device in which the flexures are located substantially below the pixel plate and at least one flexure includes a control arm. As a result of this configuration, a larger controllable pixel plate range is established. Further, the present control gap design that includes a number of control arms to form a piece-wise linear spring enables smaller pixel sizes by enabling a larger, controllable pixel displacement range for a given pixel size and/or voltage. Thus far, a light modulator device according to one exemplary embodiment has been discussed. Several other configurations are possible, including several different flexure and control arm structures and via configurations. Some of these possible configurations will now be discussed in more detail.

Alternative Embodiments

Figure 7:
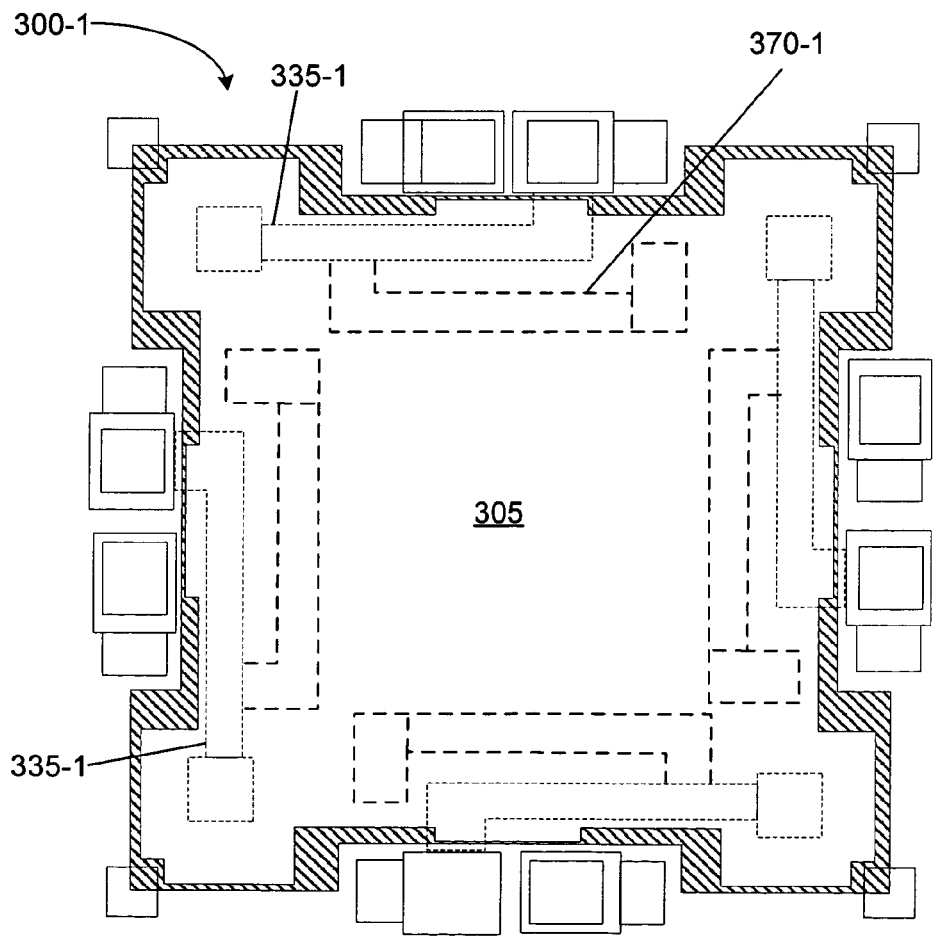
FIG. 7 illustrates a top view of a light modulator device having an elongated control arm structure, according to one exemplary embodiment.

FIG. 7 illustrates a second exemplary light modulator device (300-1) according to one exemplary embodiment. As illustrated in FIG. 7, the second exemplary light modulator device (300-1) includes a number of elongated flexures (335-1) having elongated control arms (370-1) coupled thereto. As illustrated, the elongated control arms (370-1) are coupled to the elongated flexures (335-1) near where the elongated flexures are coupled to the pixel plate (305). As mentioned previously, modifications of control arm length or the connection point of the control arm to the flexure (335-1) will vary the sensitivity of the resulting configuration to translation of the pixel plate (305). Consequently, the point at which the elongated control arm (370-1) contacts the pixel plate (305) will also vary. For example, the flexures may be between approximately 7.8 μm and 9.5 μm in length and 1.0 μm wide. The use of elongated flexures (335-1) may reduce the voltage required to operate the flexures and reduce the strain in the flexures themselves the operation of the light modulator device (300-1).

Figure 8:
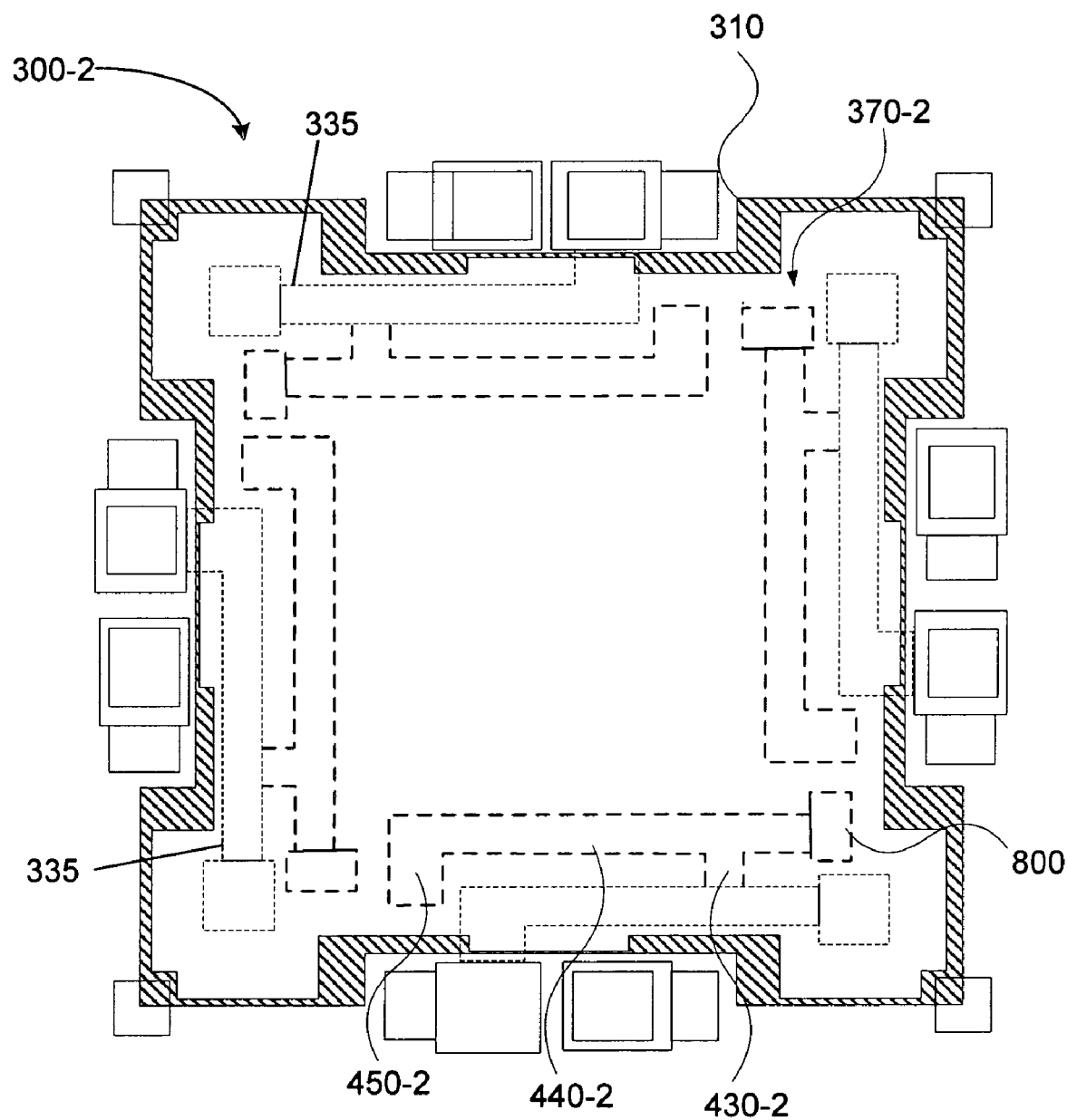
FIG. 8 illustrates a top view of a light modulator device having a control gap structure including a pull-in pad, according to one exemplary embodiment.

FIG. 8 illustrates a top cutaway view of a third exemplary light modulator device (300-2) according to one exemplary embodiment. As illustrated in FIG. 8, the third exemplary light modulator device (300-2) includes a number of flexures (335) organized in a pinwheel configuration as mentioned above. Additionally, an exemplary control arm (370-2) is coupled to each of the flexures (335). Similar to the configuration discussed above with reference to FIGS. 3 and 4, the exemplary control arms (370-2) coupled to the flexures include a control arm axis (430-2), a control arm span (440-2) oriented in substantially the same plane as the flexure (335) but extending away from the contact point of the flexure in a parallel fashion, and a pixel pate contact (450-2). However, the third exemplary light modulator device also includes a pull-in pad (800) extending from the end of the control arm span opposite the pixel plate contact (450-2). According to one exemplary embodiment, described in further detail below with reference to FIG. 9, the pull-in pad (800) is configured to be electrostatically attracted to the bottom charge plate (310).

The electrostatic attraction between the bottom charge plate (310) and the pull-in pad (800) is configured to force the control arm (370-2) up into the pixel plate (305) at a higher pixel plate position, thereby modifying the kink-position of the resulting piece-wise linear spring.

FIG. 9 further illustrates the operation of the pull-in pad (800), according to one exemplary embodiment. As illustrated in FIG. 9, the pull-in pad (800) is electrostatically attracted to the bottom charge plate (310). According to one exemplary embodiment, the pull-in pad (800) is electrically coupled to a source connection through a via. Generation and intensity of the attraction between the bottom charge plate and the pull-in pad (800) may then be selectively modified by varying the intensity levels generated by the source connection. As the electrostatic attraction is generated, the pull-in pad (800) is pulled towards the bottom charge plate (310) without making contact, which may cause a short. As the pull-in pad (800) is pulled toward the bottom charge plate (310), the control arm pivots about the control arm axis (430-2; FIG. 8) and the pixel plate contact (450) is translated closer to the pixel pate (305). Consequently, the control arm is engaged at a controllably higher pixel pate position.

In conclusion, several micro-electro mechanical (MEM) light modulator devices have been described herein that incorporate bottom mount piece-wise linear flexures resulting in relatively large pixel plates and relatively small electrostatic gaps. Consequently, the light modulator devices described herein may increase the optical performance of the device. Further, the present control gap design that includes a number of control arms to form a piece-wise linear spring enables smaller pixel sizes by enabling a larger, controllable pixel displacement range for a given pixel size and/or voltage. In addition, such a configuration allows for the use of longer flexures for a given pixel size. Longer flexures may provide lower flexure strain designs that can provide higher reliability and require lower actuation voltage.

The preceding description has been presented only to illustrate and describe the present method and apparatus. It is not intended to be exhaustive or to limit the disclosure to any precise form disclosed. Many modifications and variations are possible in light of the above teaching. It is intended that the scope of the disclosure be defined by the following claims.

What is claimed is:

1. A light modulator device, comprising:
   a bottom charge plate;
   a top plate;
   a pixel plate disposed between said top plate and bottom charge plate;
   flexures supporting said pixel plate that flex to selectively change an optical gap between said top plate and said pixel plate; and
   a piece-wise linear spring that resists flexing of said flexures beyond a predetermined point so as to resist contact between said pixel plate and said bottom charge plate.

2. The light modulator device of claim 1, wherein said piece-wise linear spring comprises at least one control arm coupled to a said flexure.

3. The light modulator device of claim 2, wherein said control arm is configured to engage said pixel plate in response to a flexing of said flexure.

4. The light modulator device of claim 2, wherein said control arm comprises:
   a control arm axis perpendicularly coupled to said flexure;
   a control arm span having a first and a second end, said control arm span being coupled to said control arm axis on said first end; and
   a pixel plate contact coupled to a second end of said control arm span.

5. The light modulator device of claim 4, wherein said pixel plate contact is not in contact with said pixel plate when said flexures are in an un-deflected state.

6. The light modulator device of claim 4, further comprising a pull-in pad coupled to said first end of said control arm.

7. The light modulator device of claim 6, wherein said pull-in pad is configured to modify a kink-position of said at least one piece-wise linear spring.

8. The light modulator device of claim 6, wherein said pull-in pad is configured to be electrostatically attracted to said bottom charge plate.

9. The light modulator device of claim 6, further comprising a via coupled to said pull-in pad;
   wherein said via is configured to selectively charge said pull-in pad.

10. The light modulator device of claim 1, further comprising:
    an electrostatic gap defined between said pixel plate and said bottom charge plate; and
    wherein said electrostatic gap is less than three times the size of said optical gap.

11. The light modulator device of claim 1, wherein said flexures are located substantially below said pixel plate.

12. The light modulator device of claim 1, further comprising at least one bump formed on an underside of said pixel plate.

13. The light modulator device of claim 12, wherein said at least one bump is configured to engage said piece-wise linear spring when said flexures flex to said predetermined point.

14. The light modulator device of claim 1, wherein said piece-wise linear spring is comprised of a plurality of linear springs.

15. The light modulator device of claim 14, wherein said plurality liner springs are arranged in a pinwheel pattern.

16. The light modulator device of claim 1, wherein:
    each said flexure comprises a span portion and a pixel plate mounting portion; and
    said piece-wise linear spring comprises at least one control arm portion including a control arm axis coupled to said flexure span portion and a control arm span.

17. The light modulator device of claim 16, wherein said flexure span portion is approximately 5.4 µm long by 1.0 µm wide.

18. The light modulator device of claim 16, wherein said flexure span portion is between approximately 7.8 and 9.5 µm long by 1.0 µm wide.

19. The light modulator device of claim 1, further comprising a plurality of first source connections, a plurality of second source connections, and a bottom oxide layer, said first source connections being coupled to said bottom charge plate and said second source connections being coupled to said pixel plate.

20. The light modulator device of claim 19, wherein a connection between each of said second source connections and said pixel plate includes an interconnect via, an intermediate charge plate, and a pixel plate via, said interconnect via extending through said bottom oxide layer and coupling said second source connection to said intermediate charge plate, and said pixel plate via coupling said intermediate charge plate to said flexures, said flexures being coupled to said pixel plate.

21. A light modulator device, comprising:
    a top plate;
    a pixel plate, wherein an optical gap between said pixel plate and said top plate is selectively controlled to control a color of light emitted by said modulator device using Fabry- Perot interference; and a pixel extension member coupled to said pixel plate and extending beyond at least one edge of said pixel plate for increasing an aperture ratio of said light modulator device with respect to said pixel plate;

wherein said pixel extension member includes a piece-wise flexure.

22. The device of claim 21, wherein said pixel extension member comprises a metallic material.

23. The device of claim 22, wherein said metallic material comprises aluminum.

24. The device of claim 22, wherein said metallic material comprises silver.

25. The device of claim 21, wherein said piece-wise flexure further comprises an oxide layer.

26. The device of claim 21, wherein said piece-wise flexure further comprises a nitride layer.

27. The device of claim 21, wherein said pixel plate comprises aluminum oxide.

28. The device of claim 21, wherein said pixel plate comprises a nitride layer.

29. The device of claim 21, wherein said pixel plate comprises an oxide layer.

30. A light modulator device, comprising:
a bottom charge plate;
a pixel plate supported a plurality of flexures, wherein said flexures are located substantially below said pixel plate;
a top plate;
a charge gap defined between said bottom charge plate and said pixel plate;
an optical gap and electrical gap defined between said top plate and said pixel plate; and
a control arm extending from said flexures, wherein said control arm is configured to not contact said pixel plate when said flexures are in a neutral position, but said control arm contacts and resists movement of said pixel plate when said flexures are flexed to a predetermined point bringing said pixel plate into contact with said control arm, said control arm resisting contact between said pixel plate and said bottom charge plate.

31. The device of claim 30, wherein said plurality of flexures each comprise:
a linear flexure; and
a control arm coupled to said linear flexure.

32. The device of claim 31, wherein said control arm is configured to engage said pixel plate in response to a flexing of said linear flexure.

33. The device of claim 31, wherein said control arm comprises:
a control arm axis perpendicularly coupled to said linear flexure;
a control arm span having a first and a second end, said control arm span being coupled to said control arm axis on said first end; and
a pixel plate contact coupled to a second end of said control arm span.

34. The device of claim 33, further comprising a pull-in pad coupled to said first end of said control arm.

35. The device of claim 34, wherein said pull-in pad is configured to be electrostatically attracted to said bottom charge plate.

36. The device of claim 30, further comprising first and second source connections coupled to said bottom charge plate.

37. The device of claim 36 wherein each of said flexures comprise a base mounting post coupled to an intermediate charge plate, said intermediate charge plate being coupled to an interconnect via, said interconnect via being coupled to a source connection, wherein said base mounting post is offset from said interconnect via.

38. The device of claim 36, wherein said top plate and said pixel plate are configured to be maintained at a substantially similar voltage level.

39. The device of claim 38, wherein a neutral state position of said pixel plate substantially corresponds to a black state value of said optical gap.

40. A display system, comprising:
a spatial light modulator having a plurality of light modulator devices, wherein at least one of said light modulator devices includes a bottom charge plate, a pixel plate supported by at least one flexure, wherein said flexure is a bimodal flexure located substantially below said pixel plate; and a top charge plate.

41. The display system of claim 40, further comprising an image processing unit coupled to said spatial light modulator.

42. The display system of claim 40, wherein an optical gap is defined between said top charge plate and said pixel plate.

43. The display system of claim 40, wherein at least one of said light modulator devices has an aperture ratio of greater than 0.75.

44. The display system of claim 40, wherein at least one of said light modulator devices has an aperture ratio of greater than 0.85.

45. The display system of claim 40, wherein at least one of said light modulator devices includes an electrostatic gap defined between said pixel plate and said bottom charge plate; and
an optical gap defined between said pixel plate and said top charge plate;
wherein said electrostatic gap is less than three times the size of said optical gap.

46. The light modulator device of claim 1, wherein said top plate is electrically non-conductive.

* * * * *

UNITED STATES PATENT AND TRADEMARK OFFICE
CERTIFICATE OF CORRECTION

PATENT NO. : 7,619,805 B2
APPLICATION NO. : 11/093835
DATED : November 17, 2009
INVENTOR(S) : Faase et al.

It is certified that error appears in the above-identified patent and that said Letters Patent is hereby corrected as shown below:

In column 12, line 36, in Claim 15, delete "liner" and insert -- linear --, therefor.

In column 13, line 2, in Claim 21, delete "Fabry- Perot" and insert -- Fabry-Perot --, therefor.

Signed and Sealed this

Sixteenth Day of March, 2010

David J. Kappos
*Director of the United States Patent and Trademark Office*